United States Patent [19]
Wang-On

[11] Patent Number: 5,234,452
[45] Date of Patent: Aug. 10, 1993

[54] EARWAX CURETTE WITH LIGHT BEAM LOCALIZING DEVICE

[76] Inventor: Kwok Wang-On, Flat D, 3rd Floor, No. 172, Wai Yip Street, Kwun Tong, Kowloon, Hong Kong

[21] Appl. No.: 942,416

[22] Filed: Sep. 9, 1992

[51] Int. Cl.⁵ .............................................. A61B 17/22
[52] U.S. Cl. ..................................... 606/160; 606/161
[58] Field of Search ............................... 606/160–162; 128/23

[56] References Cited

U.S. PATENT DOCUMENTS 4,572,180  2/1986  Deenadaylu ....................... 606/161
4,785,796  11/1988  Mattson ............................. 128/23

Primary Examiner—John D. Yasko
Assistant Examiner—William Lewis
Attorney, Agent, or Firm—Morton J. Rosenberg; David I. Klein

[57] ABSTRACT

An earwax curette includes a light beam localizing device connected to a curette body by a connecting ring to localize an incident light beam to the spoon-shaped hook of the curette body for illuminating the external auditory canal as the earwax curette is inserted in the external auditory canal to remove the earwax.

3 Claims, 4 Drawing Sheets

EARWAX CURETTE WITH LIGHT BEAM LOCALIZING DEVICE

BACKGROUND OF THE INVENTION

The present invention relates to a earwax curette and relates more particularly to a earwax curette for the removal of the earwax from the external auditory canal which is coupled with light beam localizing device for localizing an incident light beam to the spoon-shaped hook of the curette body thereof for illuminating the external auditory canal.

In removing the earwax or any foreign bodies from the external auditory canal, an earwax curette may be used. When an earwax curette is inserted in the external auditory canal to remove the earwax or any foreign bodies, the external auditory canal must be well illuminated so that the operator can clearly see the inside. However, it is inconvenient to use an external light in illuminating the external auditory canal. Closing an external light to the ear for illuminating the external auditory canal well may produce an intensive heat causing the ear hot.

SUMMARY OF THE INVENTION

The present invention has been accomplished under the aforesaid circumstances. According to one aspect of the present invention, the earwax curette is made from a light transmitting material which automatically localizes an incident light beam collected by a light beam localizing device to the spoon-shaped hook of the curette body thereof for illuminating the external auditory canal as the earwax curette is inserted in the external auditory canal to remove the earwax. According to another aspect of the present invention the light beam localizing device can be rotated through 360° angle on the curette body to collect light beams from all directions. According to still another aspect of the present invention, the light beam localizing device can be made in any of a variety of shapes and angles for use in different situations.

DETAILED DESCRIPTION OF THE PREFERRED EMBODIMENTS

Figure 1:
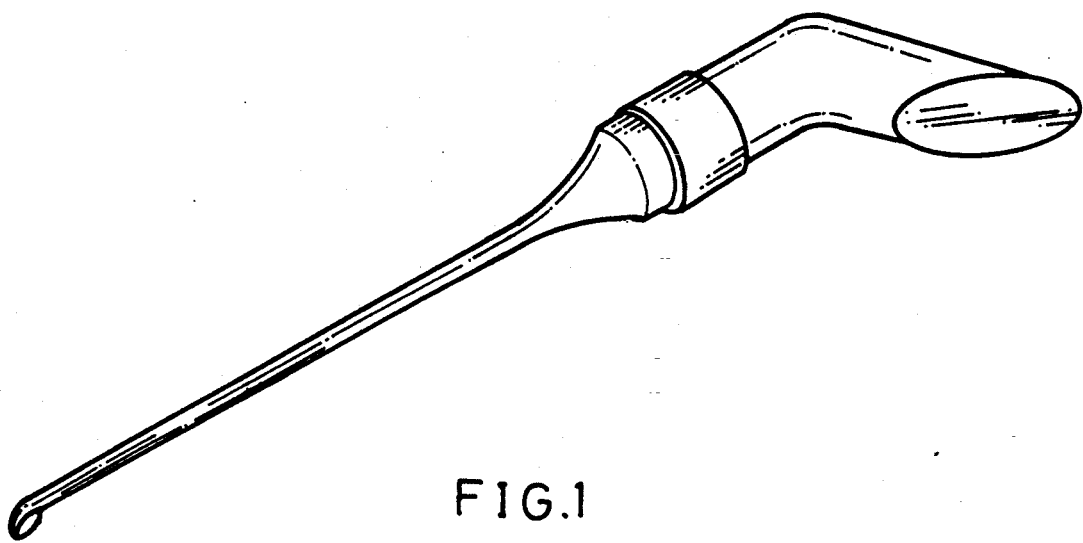
FIG. 1 is an elevational view of a earwax curette embodying the present invention.
Figure 2:
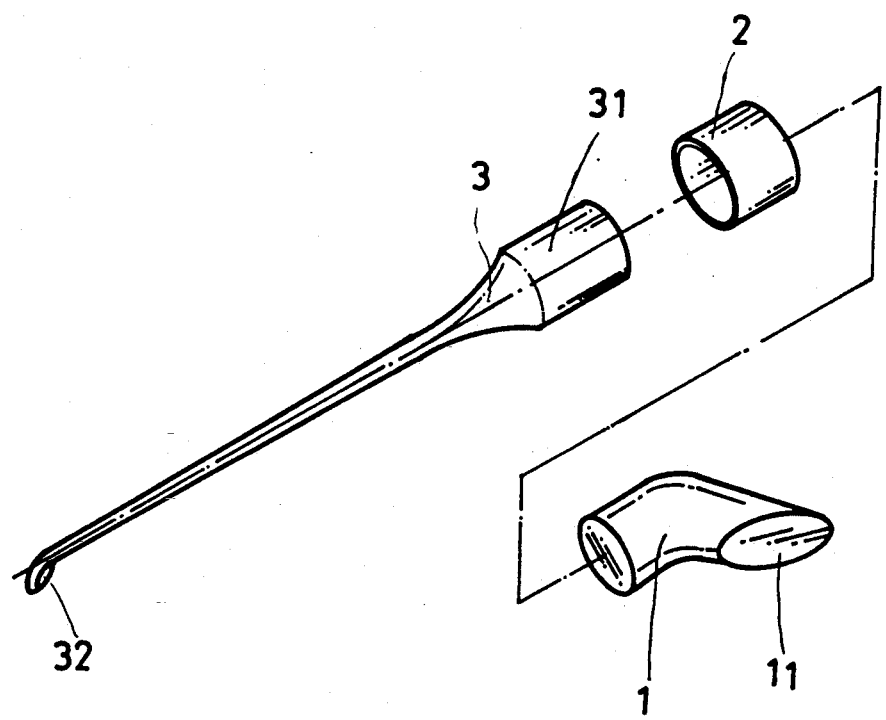
FIG. 2 is an exploded view of the earwax curette of FIG. 1.

Referring to FIGS. 1 and 2, a earwax curette as constructed in accordance with the present invention is generally comprised of a light beam localizing device 1, a connecting ring 2 and a curette body 3, which are respectively made from a light transmitting material. The light beam localizing device 1 has a bottom end inserted into the connecting ring 2 and a top end formed into a sloping light collecting surface 11 for collecting the light from an external light source. The curette body 3 has a top connecting end 31 inserted into the connecting ring 2 from the opposite end. By means of the connecting ring 2, the light beam localizing device 1 is connected to the curette body 3 on the top.

Figure 3:
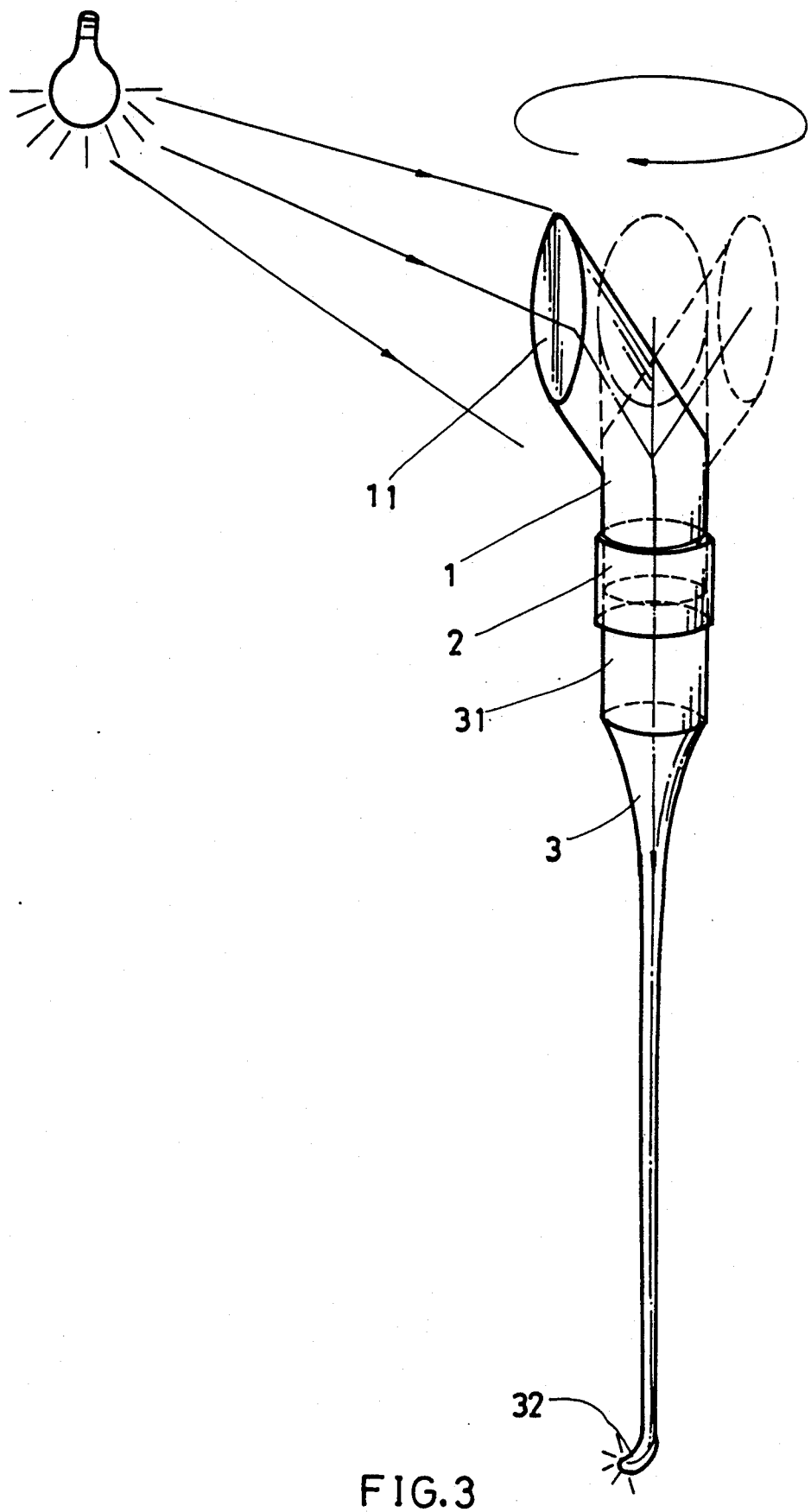
FIG. 3 is a pictorial drawing showing the operation of the present invention in localizing a light beam.

Referring to FIG. 3, the light beam localizing device 1 can be rotated on the curette body 3 through 360° angle so that the sloping light collecting surface 11 can be moved toward the light source to collect light. The incident light beam which pass through the sloping light collecting surface 11 is transmitted to the curette body 3 and localized to the spoon-shaped hook 32 on the bottom end of the curette body 3 for illuminating the external auditory canal, so as to facilitate the removal of the earwax by the earwax curette.

Figure 4:
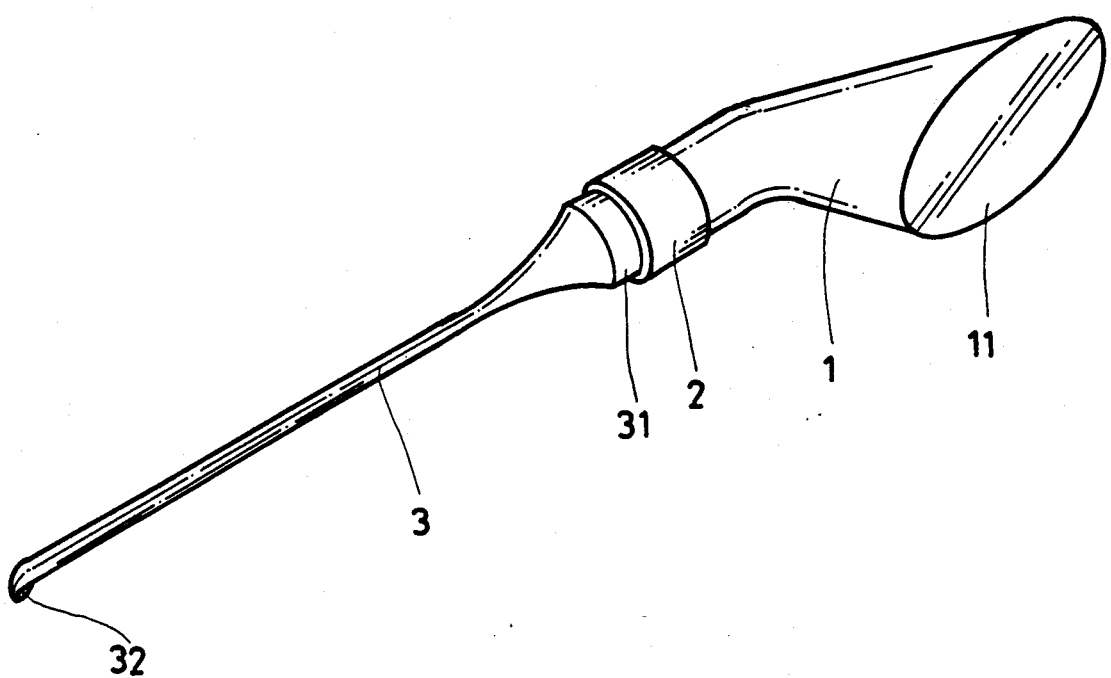
FIG. 4 is an alternate form of the foreign body curette according to the present invention.

Referring to FIG. 4, therein illustrated is an alternate form of the earwax curette. In this alternate form, the light beam localizing device 1 is gradually expanded upwards. Therefore, a wide area of sloping light collecting surface 11 is provided for gathering much light.

Figure 5:
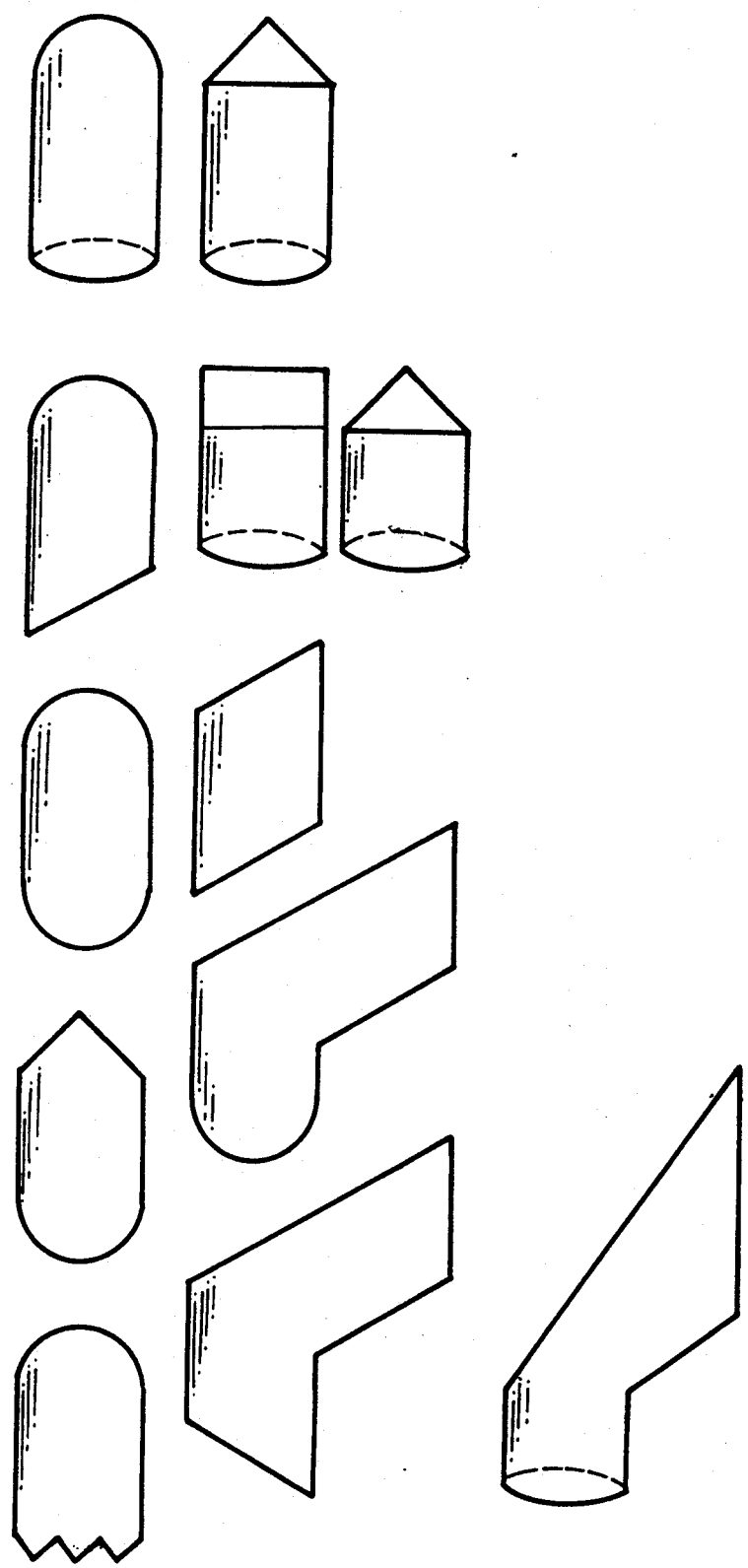
FIG. 5 illustrates a wide variety of light beam localizing devices according to the present invention.

Referring to FIG. 5, the light beam localizing device 1 may be made in any of a variety of shapes for alternative use in different situations in collecting light from any of a variety of external light sources.

As indicated, the present invention is to provide a earwax curette which uses a light beam localizing device to collect and transmit a light beam to the spoon-shaped hook of the curette body thereof for illuminating the external auditory canal, wherein the light beam localizing device can be rotated on the curette body through 360° angle to fit the incident light beam. Because the earwax curette is made from a light transmitting material, it can effectively collect and localize the light of a light source at distance so that the heat from the light source can be isolated.

What is claimed is:

1. An earwax curette comprising:
   (a) a light beam localizing member for collecting an transmitting visible light, said light beam localizing member having an upper end section including a light collecting surface and a lower end section;
   (b) a curette body member formed of a light transmitting material composition having an upper end section mounted adjacent said lower end section of said light beam localizing member and a lower end section terminating in a spoon contoured hook member;
   (c) a connecting ring member coupled to said upper end section of said curette body member, said lower end section of said light beam localizing member being insertable within said connecting ring member and rotatable therein, whereby said light beam localizing member may be rotated within said connecting ring member for selectively positioning said light collecting surface with respect to an external light source for maximizing light to said spoon contoured hook member and illuminating an external auditory canal area.

2. The earwax curette as recited in claim 1 wherein said light beam localizing member lower end section extends in a vertical direction and said upper end section extends in a direction inclined with respect to said vertical direction.

3. The earwax curette as recited in claim 1 where said light collecting surface of said light beam defines a substantially planar surface, said planar surface being inclined with respect to an extension length direction of said light beam localizing member upper end section.

* * * * *